United States Statutory Invention Registration [19]

[11] Reg. Number: H819

Srivastava et al. [43] Published: Sep. 4, 1990

[54] PALLADIUM-109 LABELED ANTI-MELANOMA MONOCLONAL ANTIBODIES

[75] Inventors: Suresh C. Srivastava, Setauket; Rashid A. Fawwaz, Pelham; Soldano Ferrone, Scarsdale, all of N.Y.

[73] Assignee: The United States of America as represented by the Secretary of Energy, Washington, D.C.

[21] Appl. No.: 605,439

[22] Filed: Apr. 30, 1984

[51] Int. Cl.[5] ..... A61K 43/00; A61K 39/395

[52] U.S. Cl. ..... 530/389; 424/1.1; 424/9; 435/106; 435/108; 436/548

[58] Field of Search ..... 424/1.1, 9; 436/548; 435/106–108

[56] References Cited

U.S. PATENT DOCUMENTS

| | | | |
|---|---|---|---|
| 4,444,744 | 4/1984 | Goldenberg | 424/1.1 |
| 4,452,774 | 6/1984 | Jones | 424/1.1 |
| 4,472,509 | 9/1984 | Gansow et al. | 436/548 |
| 4,500,508 | 2/1985 | Srivastava et al. | 424/1.1 |

OTHER PUBLICATIONS

Fawwaz et al., J. Nucl. Med., 25:796–9, (1984).
Krejcarek et al., Biochem. Biophys. Res. Comm., 77(2), 581–5, (1977).
Hnatowich et al., Int. J. Appl. Rad. Isotopes, 33, 327–32, (1983).
Natali et al., J. Nat. Cancer Inst., 67(3), 591–601, (1981).
Wilson et al., Int. J. Cancer, 28, 293–300, (1981).
Sfakianakis et al., J. Nucl. Med., 23, 840–50, (1982).
Goldenberg, J. Nucl. Med., 24(4), 360–62, (1983).
Larson et al., J. Nucl. Med., 24, 123–129, (1983).
Sundberg et al., J. Med. Chem., 17(12), 1304–7, (1974).
Meares et al., Proc. Natl. Acad. Sci., U.S.A., 73(11), 3803–6, (1976).
Scheinberg et al., Science, 215, 1511–3, (1982).
Halpern et al., J. Nucl. Med., 23, p. 8, (May, 1982).
Order et al., Cancer Research, 40, 3001–7, (1980).
Fawwaz et al., J. Nucl. Med., 24(5), p. 78, (May 1983).
Matzku et al., Chemical Abstracts, 99, (1983), #84512y.
Imai et al., Chemical Abstracts, 99, (1983), #205742j.
CRC Handbook Series in Clinical Laboratory Science, Section A: Nuclear Medicine, vol. II, CRC Press, Inc., Boca Raton, Fla., (1982), p. 147.

*Primary Examiner*—John F. Terapane
*Assistant Examiner*—Valerie Fee
*Attorney, Agent, or Firm*—Margaret C. Bogosian; Paul A. Gottlieb; Judson R. Hightower

[57] ABSTRACT

Palladium-109, a beta-emitting radionuclide, when chelated to anti-melanoma monoclonal antibody demonstrates high uptake in melanoma and thus is useful for tumor therapy.

4 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

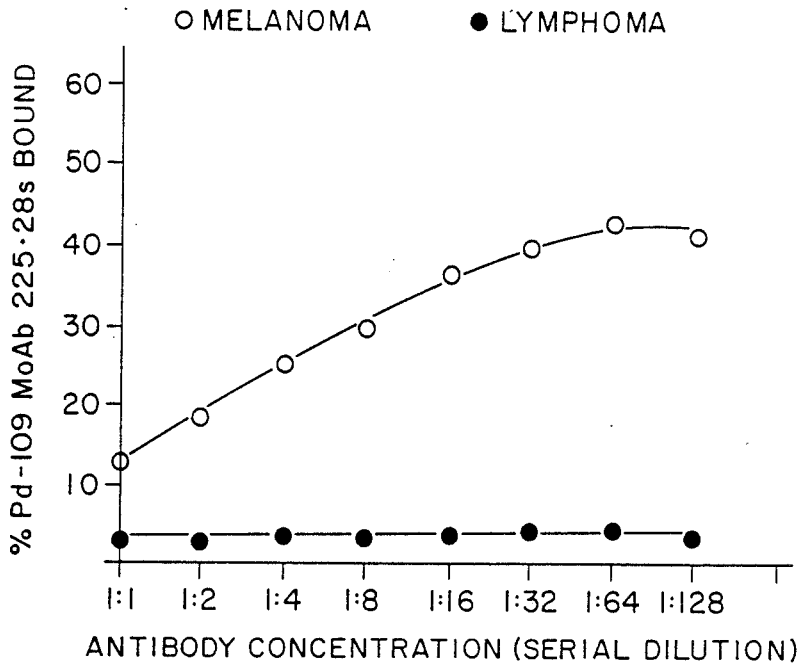
O MELANOMA
● LYMPHOMA
% Pd-109 MoAb 225·28s BOUND
60
50
40
30
20
10
1:1
1:2
1:4
1:8
1:16
1:32
1:64
1:128
ANTIBODY CONCENTRATION (SERIAL DILUTION)

PALLADIUM-109 LABELED ANTI-MELANOMA MONOCLONAL ANTIBODIES

The U. S. Government has rights in this invention pursuant to Contract Number DE-AC02-76CH00016, between the U.S. Department of Energy and Associated Universities Inc.

BACKGROUND OF THE INVENTION

Recently, monoclonal antibodies labeled with the radionuclide iodine-131 have been used for the detection of tumors. Goldenberg reported the imaging of tumors using monoclonal antibodies [*Journal of Nuclear Medicine,* 24, 360–362 (1983)] while Larson, et al. reported melanoma imaging using iodine-131 labeled monoclonal antibodies [*Journal of Nuclear Medicine,* 24, 123–129 (1983)]. One of the problems that has been encountered with such radionuclide labeled monoclonal antibodies has been that the labeling inactivates the antibody because the radionuclide attaches at or near the antigen-binding sites. One approach to overcoming this problem is to employ bi-functional chelates that are capable of covalently binding to the antibody and also complexing with a metallic radionuclide. Krejcarek, et al. discuss the covalent attachment of chelating groups to macromolecules, [*Biochemical and Biophysics Research Communications,* 77, 581–585 (1977)].

DESCRIPTION OF THE DRAWING

The Figure shows the in vitro binding of palladium-109 labeled anti-Human High Molecular Weight Melanoma Associated Antigen Monoclonal Antibody 225.28S to human COLO 38 melanoma cells and to lymphoma cells in times culture.

DETAILED DESCRIPTION OF THE INVENTION

The present invention consists of new radiolabeled monoclonal antibodies, the method of preparing these material, and there use in the radiotherapy of melanoma. More specifically the present invention is directed to the use of anti-melanoma monoclonal antibodies which have been chelate-conjugated and radiolabeled as carriers of radioactivity to the site of a tumor for the purpose of inducing tumor therapy.

The radionuclide employed is palladium-109, which is a predominantly beta-emitting radionuclide with a half-life of 13.4 hours, a beta emission of 1.028 MeV maximum, and a scatter area of 2 mm. Palladium-109 is available in meaningful quantities and can be obtained in almost carrier-free form, a necessity for human application. The palladium-109 that has been used in the experimental work discussed herein has been produced at the High Flux Beam Reactor (HFBR) at Brookhaven National Laboratory. This material exhibits a specific activity at the end of bombardment of approximately 1 Curie per milligram. For future human application, it is intended that the palladium-109 radionuclide will be produced at the Brookhaven Linac Isotope Production Facility (BLIP). The material that will be produced at the BLIP will exhibit higher specific activity and will be essentially carrier free.

The bifunctional chelate employed is diethylenetriamine pentaacetic acid (DTPA) which can be coupled to the monoclonal antibody using several different synthetic approaches. One approach involves the use of mixed anhydrides and this synthetic method has been reported by Krejcarek, et al. in a paper entitled "Covalent Attachment of Chelating Groups to Macromolecules", *Biochemical and Biophysical Research Communications,* 77 581–585 (1977). The second approach to linking the DTPA to the monoclonal antibody is the cyclic anhydride approach reported by E. Kehuan, et al., *Journal of Pharmacological Science,* 64, 704–706 (1975), and by Hnatowich, et al. in "Radioactive Labeling of Antibody: A Simple and Efficient Method", *Science,* 220, 613–615 (1983). The cyclic anhydride approach for the preparation of the chelate-conjugated monoclonal antibodies of the present invention is preferred. Other chelating agents may be used in place of the DTPA. For example, several polyamine-carboxylate compounds, 8-hydroxy quinoline and its derivatives, dimethylglyoxime, and desferrioxamine, are also suitable chelating agents for conjugation to the monoclonal antibody for attaching the metallic radionuclide palladium-109.

The monoclonal antibodies employed in the present invention are a family of antibodies to human high molecular weight melanoma associated antigens. This family of monoclonal antibodies contains six distinct antibodies designated by the following identifying numbers: 138.13S, 225.28S, 653.40S, 763.24T, 376.96S, and 465.12S. Several of these antibodies recognize one determinant while others recognize more than one. The high degree of heterogeneity exhibited by the tumor can be overcome to some extent by using a combination of several of the above monoclonal antibodies which will then recognize various antigens or determinants. The preparation of the monoclonal antibody 653.40S is reported by Ferrone, et al. in the *Journal of the National Cancer Institute,* 67, 591–601 (1981). The preparation of the monclonal antibodies 225.28S and 465.12S is reported by Ferrone, et al. in the *International Journal of Cancer,* 28, 293–300 (1981). The other members of this monoclonal antibody family are prepared following the procedures and purification methods reported in both of the cited Ferrone, et al. papers.

It has been discovered that palladium-109 when chelated to anti-melanoma monoclonal antibodies demonstrates high uptake in human melanoma. Therefore, these novel palladium-109 labeled, chelate conjugated monoclonal antibodies are therapeutically useful for tumor therapy. It is recognized that the tumor therapy attributes of the material might also be substantially enhanced by using antibody fragments to increase blood clearance, decrease bone marrow toxicity, and to decrease normal tissue uptake.

The palladium-109 labeled monclonal antibodies of the present invention are useful in the therapeutic treatment of tumors. For this purpose, the mammalian subject in need of such therapeutic treatment may be treated with the palladium-109 labeled material by administration of this material through intravenous infusion. The palladium-109 labeled monoclonal antibodies may be infused very slowly, preferably over a period of about one hour, as pure material or they may be diluted with saline or dextrose for infusion. The administration regimen to be followed will depend on the individual patient. In general, about 150 millicuries bound to 100 μg–2 mg of the antibody should provide the therapeutic dose for most human patients. The palladium-109 labeled monoclonal antibodies will upon administration seek out the site of the melanoma and deliver to the tumor the prescribed dose of radiation. These radiopharmaceutical compositions will seek out both the primary and secondary melanoma sites, that is the primary site of the tumor and any secondary sites resulting from metastasis.

EXAMPLE 1

Preparation of the Monoclonal Antibodies

Hybridomas were constructed with the murine myeloma cell line Sp2/0-Ag-14 and splenocytes from mice immunized with the melanoma cell line M21 as described in Ferrone, et al., *Transplantation Proceedings*, 12, 380–383 (1980). The hybridomas secreting the monoclonal antibody 225.28S have been subcloned and propagated in vitro and in vivo. The monoclonal antibody 225.28S is cell membrane reactive.

Following exactly the same procedure as described above, the monoclonal antibody 465.12S was also prepared. This monoclonal antibody is cytoplasm reactive. Both the 225.28S and 485.12S monoclonal antibodies are of the IgG2a subclass and were purified from mouse ascites fluid by adsorption/elution from protein A Sepharose 4B (purchased from Pharmacia, Piscataway, N.J.).

Following the specific procedures described above, the monoclonal antibody 653.40S was also prepared. This monoclonal antibody falls into the IgGI subclass.

EXAMPLE 2

Preparation of the Monoclonal Antibody - DTPA Conjugate

Two methods were used for conjugating DTPA to the antibody; the mixed anhydride method and the cyclic anhydride method. In the latter method, the DTPA anhydride was added to the antibody at a pH of 7.0 (HEPES, 0.05M) and incubated for 30 minutes at room temperature. The antibody concentration was kept between 0.2 and 1.5 milligrams per milliliter, and the ratio of anhydride to antibody was either 1:1 or 10:1. The resulting mixture was dialyzed against two one-liter batches of 0.05M HEPES (pH 7.0) at 4° C. for two days. In the mixed anhydride method, a 300 to 2000 fold excess of the anhydride was added to the antibody at a pH of 7 to 8 (0.1M $NaHCO_3$) and incubation carried out at 4° C. overnight. The protein concentration varied between 0.2 and 1.5 milligrams per milliliter. The mixture was then dialyzed against two one-liter batches of a 0.1M acetate buffer, pH 5.0 (or with 0.1M glycine/HCl buffer at pH 3.5) at 4° C. for two days.

EXAMPLE 3

Labeling of the Chelate Conjugated Monoclonal Antibody With Palladium-109

Palladium-109 chloride was prepared by bombarding palladium-108 chloride in a sealed quartz ampule in the Brookhaven High Flux Beam Reactor ($8\times10^{14}$n $s^{-1}cm^{-2}$) for 24 hours. Typically, approximately two milligrams of palladium as palladium-108 chloride provided over two Curies of palladium-109 at the end of bombardment. The material was dissolved in either 2.0 milliliters DMSO or in 1 ml of a 0.1M pH5 acetate buffer by gentle heating and stirring. An aliquot of this solution (10–20 μl) was transferred into a 10 ml multi-injection bottle containing 1 ml of a pH 5.0, 0.1M acetate buffer and 0.3 ml of the monoclonal antibody DTPA conjugate (1.43 mg/ml in acetate buffer). The mixture was incubated at 37° for two hours and then applied onto a 0.9×100 cm Sephadex G-150 column for purification. The eluting buffer consisted of 0.05 M HEPES, pH 7.0. The radioactivity of the fraction was assayed using a dose calibrator and the appropriate fractions combined and concentrated to reduce the volume. This column method provided an effective separation of the desired palladium-109 labeled monoclonal antibody DTPA conjugate from unwanted impurities found in the preparation. The yield varied between 6 and 10 percent depending on the amount of palladium-109 used and the amount of the monoclonal antibody DTPA solution. The specific activity of these preparations was 0.6–1.0 μCi of palladium-109/μg protein. The labeling yields and the specific activity of the preparations can be increased much further by employing carrier-free palladium-109.

EXAMPLE 4

In Vitro Binding Assay: To determine the melanoma binding affinity of the Pd-109 labeled anti-melanoma monoclonal antibody, cultured COLO-38 human melanoma cells were incubated for one hour at room temperature with the radiolabeled antibody. Cultured human lymphoma cells incubated in a similar manner were used as a control. The cells were washed three times and the binding of antibody to cells was determined in triplicate at antibody dilutions ranging from 1:1 to 1:128.

TABLE 1

Percent of Administered Pd-109 MoAb 225.28s Per Gram Tissue

| | Hours Post Injection | | |
|---|---|---|---|
| | 13 | 24 | 48 |
| Blood | 0.50 ± 0.03 | 0.51 ± 0.04 | 0.30 ± 0.04 |
| Tumor | 19.99 ± 0.54 | 19.51 ± 1.46 | 18.51 ± 2.11 |
| Lung | 1.46 ± 0.07 | 0.94 ± 0.12 | 0.64 ± 0.05 |
| Liver | 5.04 ± 0.41 | 4.54 ± 0.44 | 4.26 ± 0.18 |
| Spleen | 2.69 ± 0.16 | 3.15 ± 0.40 | 3.01 ± 0.11 |
| Kidney | 13.67 ± 0.46 | 11.15 ± 1.50 | 10.05 ± 1.16 |
| Muscle | 0.51 ± 0.05 | 0.55 ± 0.29 | 0.32 ± 0.07 |
| Bone | 1.35 ± 0.08 | 1.48 ± 0.18 | 1.31 ± 0.14 |

Tumor Cell Lines: Human melanoma cells (COLO-38) were cultured in RPMI 1640 medium with L-glutamycin. Solid tumors were produced in athymic nude mice (Swiss/Webster,nu/nu) by injection of $10^7$ melanoma cells in the flank. The tumors were allowed to reach a size of approximately 5 mm in diameter prior to experimentation.

In Vitro Binding of Pd-109-MoAB 225.28S to Melanoma: FIG. 1 demonstrates that Pd-109-MoAB 225.28S achieved significantly ($P < 0.001$) higher melanoma cell binding in tissue culture (41.3% in the plateau region) than with control lymphoma cells (3.1%).

EXAMPLE 5

In Vivo Binding of Palladium-109 Monoclonal Antibody 225.28S to Melanoma Tumor Three groups of athymic nude mice bearing COLO 38 human melanoma tumor (n=3–6/group) were injected with 10 μCi of Pd-109-MoAb 225.28S and sacrificed 13,24 and 48 hours later, respectively, for determination of radioactivity (% injected dose/g). As shown in Table 1, the concentration of Pd-109 MoAb 25.28S in melanoma at different periods after administration of radioactivity was uniformly higher ($P < 0.001$) than achieved in other tissues.

Decreased liver and renal uptake and enhanced tumor to background ratios can be achieved by using carrier free palladium-109, increasing the binding efficiency (under different conditions and using other chelating agents) of palladium-109 to antibody, and by using antibody fragments labeled with palladium-109.

We claim:

1. A radiopharmaceutical composition consisting of the monoclonal antibodies to human high molecular weight melanoma associated antigens, or fragments of said antibodies which are chelate-conjugated and labeled with palladium-109.

2. The composition of claim 1 wherein the monoclonal antibody is MoAb 225.28S.

3. The composition of claim 1 wherein the chelate component is diethylenetriaminepentaacetic acid (DTPA).

4. A radiotherapeutic method of treating melanoma by the intravenous infusion of a radiopharmaceutical composition consisting of an antibody to human high molecular weight melanoma associated antigens, or a fragment of said antibody, which is chelate-conjugated and labeled with palladium-109.

* * * * *